United States Patent
Suvaci

(10) Patent No.: US 11,608,275 B2
(45) Date of Patent: Mar. 21, 2023

(54) METHOD FOR PRODUCING ZINC OXIDE PLATELETS WITH CONTROLLED SIZE AND MORPHOLOGY

(71) Applicant: ENTEKNO ENDUSTRIYEL TEKNOLOJIK VE NANO MALZEMELER SANAYI VE TICARET ANONIM SIRKETI, Eskisehir (TR)

(72) Inventor: Ender Suvaci, Eskisehir (TR)

(73) Assignee: ENTEKNO ENDUSTRIYEL TEKNOLOJIK VE NANO MALZEMELER SANAYIVE TICARET ANONIM SIRKETI, Eskisehir (TR)

( * ) Notice: Subject to any disclaimer, the term of this patent is extended or adjusted under 35 U.S.C. 154(b) by 222 days.

(21) Appl. No.: 16/643,870

(22) PCT Filed: Sep. 13, 2017

(86) PCT No.: PCT/TR2017/050429
§ 371 (c)(1),
(2) Date: Mar. 3, 2020

(87) PCT Pub. No.: WO2019/054954
PCT Pub. Date: Mar. 21, 2019

(65) Prior Publication Data
US 2020/0247684 A1    Aug. 6, 2020

(51) Int. Cl.
*C01G 9/02* (2006.01)
*A61K 8/02* (2006.01)
*A61K 8/27* (2006.01)

(52) U.S. Cl.
CPC .............. *C01G 9/02* (2013.01); *A61K 8/0254* (2013.01); *A61K 8/27* (2013.01); *C01P 2002/52* (2013.01);
(Continued)

(58) Field of Classification Search
CPC .............. C01P 2004/11; C01P 2004/22; C01P 2004/45; C01P 2004/50; C01P 2004/80;
(Continued)

(56) References Cited

U.S. PATENT DOCUMENTS

| 4,544,761 A | 10/1985 | Taylor et al. |
| 2001/0051137 A1* | 12/2001 | Miyata .................. A61Q 17/04 424/59 |

(Continued)

FOREIGN PATENT DOCUMENTS

| CN | 101016164 A | 8/2007 |
| EP | 2233434 A1 | 9/2010 |

(Continued)

OTHER PUBLICATIONS

Jood et al., Al-Doped Zinc Oxide Nanocomposites with Enhanced Thermoelectric Properties, Nano Lett. 2011, 11, 4337-4342 (Year: 2011).*

(Continued)

*Primary Examiner* — Hoa (Holly) Le
(74) *Attorney, Agent, or Firm* — Bayramoglu Law Offices LLC

(57) ABSTRACT

A method for producing polygonic Zn oxide platelets having a median specific surface area of more than 25 square meters per gram, in controlled size and morphology, the method comprising: preparing a medium including Zn or its compounds at a concentration within the range between 1.55 and 7.75 moles of Zn/L, in a medium suitable to substitute Zn ions by releasing free protons thereby forming a complex structure including Zn; agitation of the medium in a vessel at a temperature within the range between 50 and 320° for a duration up to 10 hours to obtain a suspension; filtering the suspension to obtain a filtrate including solid particles; drying and then calcination of the dried filtrate; wherein the (Continued)

agitation is performed with one or more radial flow impellers so that the Reynolds' number in the vessel is higher than 2500 and lower than 10000.

20 Claims, 18 Drawing Sheets

(52) U.S. Cl.
CPC ...... *C01P 2004/22* (2013.01); *C01P 2006/12* (2013.01); *C01P 2006/22* (2013.01)

(58) Field of Classification Search
CPC .............. C01P 2004/82; C01P 2006/12; C01P 2006/60
USPC .......................................... 428/402; 423/622
See application file for complete search history.

(56) References Cited

U.S. PATENT DOCUMENTS

| | | |
|---|---|---|
| 2008/0254295 A1 | 10/2008 | Hibst et al. |
| 2010/0119829 A1 | 5/2010 | Karpov et al. |
| 2010/0284893 A1* | 11/2010 | Richards .................. C30B 7/06 423/437.1 |
| 2014/0050925 A1* | 2/2014 | Sueda ..................... C09C 1/043 423/622 |
| 2014/0142213 A1* | 5/2014 | Weiss ..................... A61K 33/30 523/122 |
| 2016/0004177 A1 | 1/2016 | Chiba et al. |
| 2017/0044022 A1 | 2/2017 | Yoshikawa et al. |
| 2017/0065506 A1* | 3/2017 | Gershon ................. A61Q 17/04 |

FOREIGN PATENT DOCUMENTS

| | | | |
|---|---|---|---|
| EP | 2703352 A1 | 3/2014 | |
| EP | 3326975 A1 * | 5/2018 | ............ A01N 59/00 |
| TR | 200907209 A1 | 4/2011 | |

OTHER PUBLICATIONS

Oves et al., Anti-microbial activity of cobalt doped zinc oxide nanoparticles: Targeting water borne bacteria, http://dx.doi.org/10.1016/j.jscs.2015.05.003 1319-6103 $^a$ 2015 The Authors. Production and hosting by Elsevier B.V. on behalf of King Saud University. (Year: 2015).*

Samanta et al., Chemical growth of hexagonal zinc oxide nanorods and their optical properties, Appl Nanosci (2012) 2:111-117 DOI 10.1007/s13204-011-0038-8 (Year: 2012).*

Polarz et al., Preparation of High-Surface-Area Zinc Oxide with Ordered Porosity, Different Pore Sizes, and Nanocrystalline Walls, Chem. Eur. J. 2007, 13, 592-597 (Year: 2007).*

Xianbiao Wang, et al., Mass production of micro/nanostructured porous ZnO plates and their strong structurally enhanced and selective adsorption performance for environmental remediation, Journal of Materials Chemistry, 2010, pp. 8582-8590, 20.

Arnab Kanti Giri, et al., Rectangular ZnO porous nano-plate assembly with excellent acetone sensing performance and catalytic activity, The Royal Society of Chemistry, 2015, pp. 102134-102142, 5.

Santosh S. Patil, et al., Nanostructured microspheres of silver @ zinc oxide: an excellent impeder of bacterial growth and biofilm, J Nanopart Res, 2014, 16:2717.

Ba-Abbad Muneer M., et al., Visible light photocatalytic activity of Fe3+-doped ZnO nanoparticle prepared via sol-gel technique, Chemosphere, 2013, pp. 1604-1611, 91.

Hailong Dong, et al., Porous ZnO platelets via controlled thermal decomposition of zinc glycerolate, Journal of Alloys and Compounds, 2012, pp. 125-129, 513.

Annika Vogt, et al., 40 nm, but not 750 or 1,500 nm, Nanoparticles Enter Epidermal CD1a+ Cells after Transcutaneous Application on Human Skin, Journal of Investigate Dermatology, 2006, pp. 1316-1322, 126.

* cited by examiner

METHOD FOR PRODUCING ZINC OXIDE PLATELETS WITH CONTROLLED SIZE AND MORPHOLOGY

CROSS REFERENCES TO THE RELATED APPLICATIONS

This application is the national phase entry of International Application No. PCT/TR2017/050429, filed on Sep. 13, 2017, the entire contents of which are incorporated herein by reference.

TECHNICAL FIELD

The present invention relates to size and morphology-controlled obtainment of Zinc oxide particles. In particular, the present invention relates to obtainment of polygonic Zn oxide platelets having a high median specific surface area.

BACKGROUND

Studies on nanostructures, enable production of equipment that facilitate the human life, such as dirt-repellent paints, antimicrobial structures, water-repellent surfaces, active UV (ultraviolet lights) protectors, small-sized electronic instruments, etc.

Yet, nanostructures have the potential to present some disadvantages due to extremely small size thereof. One of such disadvantages arises from the fact that their surface energy very high due to their size. Nano structures present the tendency to form agglomerates in an uncontrolled fashion in order to reduce the extent of their surface energy. As a result, the structure takes the form of micron-sized agglomerate. The decrease of surface energy complicates the use of the structures, and also causes disappearance of unique characteristics observed in nanoscale.

Nanostructures can pass through micro filters used for protection from particles in the air. Furthermore, a study conducted by Vogt et al. (2006) revealed that particles of 40 nm diameter can pass through the skin, since the diameter of the pores at the "stratum corneum", the uppermost layer of the skin, is approximately 80 nm. Therefore, the size of the nanostructure should be 80 nm at minimum in order to prevent transcutaneous penetration, thus threaten human health. Hence nanostructures can also penetrate into the human skin through transcutaneous ways, and thereby contaminate the blood stream so that easily reaches to the lungs or the digestive system, where they might induce production of free radicals that damages the cells and the DNA structure. Nanostructures can further access into the blood cells and easily penetrate thereinto thereby infiltrating to the immunity system to induce permanent damages at nerve cells and even at the brain.

Nanostructures are also known for being harmful to the environment and the nature, e.g. in case when they contaminate the soil. Therefore, development of novel solutions is required as regards safe use of the nanostructures while benefiting from their unique and outstanding properties.

Zinc oxide, which is available in form of nanostructures, presents antihistaminic, anti-erythema features and it is known for its ability to protect against UV light. Zinc oxide can also be used in the field of decontamination (neutralization of hazardous chemicals as a result of chemical reaction). Accordingly, zinc oxide (ZnO) can be employed in the fields such as decontamination of polluted waters, neutralization of chemical warfare agents and the chemical residues that remain in the soil after fertilization, and removing the chemicals from the soil and the plants. Zinc oxide also presents semi-conductive features, and has a vast potential for technical use and for research purposes.

Zinc oxide is employed in various technologies involving materials that can penetrate through the human skin directly or affect the human beings indirectly, such as in water treatment, thereby being a potential threat to the human health. Likewise, if used in the form of nanoparticles for the purpose of decontaminating the soil, it is possible that it can accumulate at the root tips and/or penetrate into, and damage, respective plant cells.

Optical and chemical properties of the zinc oxide nanostructures are better compared to the micron-sized zinc oxide structures. However, such type of nanostructures is applied directly to the human skin considering, in particular, its use for sunscreens, medical powders, healthcare ointments and decontamination of hazardous warfare gases. Although zinc oxide (ZnO) is considered as a very important material for such applications by virtue of its optical and chemical properties, use of nano-sized zinc oxide (ZnO) structures for such purposes is rather not appropriate based on the fact that it is also a structure with toxic properties as it might penetrate through the human skin and mix into the blood stream. Moreover, the structure might achieve micron size by strong and uncontrolled random agglomeration, and thereby losing their unique behavior it shows in nanoscale.

In order to prevent the above mentioned potential detrimental effects on human health, generally organic or polymeric coatings are applied to the nanostructures, thereby increasing the size thereof, to prevent them from being penetrated into the cell structure. This method, however, covers the surface of the basic nanostructure and blocks its active characteristics expected from a nanoparticle.

Another practice for preventing toxic characteristics of the nanostructures is to endeavor to maintain the size of the particles over a certain level. In this approach, nanostructures shall be large enough to avoid dermal penetration, thus cannot reach to the cellular structures and the blood, eliminating its toxic characteristics.

Another problem experienced with inorganic structures such as zinc oxide (ZnO) particles is their opacity, which starts to disappear as the size of the particles are reduced to nanoscale. This fact might be important for products such as sunscreens, moisturizers, etc. which are prominent in the field of cosmetics.

In the embodiments available in the prior art, the most suitable grain size is indicated to be below 50 nm for optical and chemical practices for zinc oxide (ZnO). Such grain size, however, is hazardous for practices on the human skin since it is smaller than the above mentioned size of pores on the human skin.

In applications of zinc oxide such as cosmetic creams and ointments, transparent electrical conductive oxides, antimicrobial substances and water treatment due to its photocatalytic properties, zinc oxide is used as coating over respective surfaces. In order to be able to cover the surface in such applications, using lesser amount of substance and as to be transparent, if desired, the materials used should have be in nanoscale, have large surface area and present a geometrical shape capable of ensuring effective coverage performance. In line with this, a production method that would ensure achievement of ZnO micro platelets to be formed by agglomeration of nano-sized particles with designed geometry, large surface area and high covering ability, is required.

The document EP 2 703 352 A1 discloses synthesis of hexagonal platelet shaped zinc oxide particles for cosmetic applications. However, the sizes of the platelets are mostly less than 200 nm and hence they are generally nanosized platelets of ZnO which can still penetrate to the skin. Agglomeration remains still an issue with sizes around 200 nm, which leads to decrease in surface area per unit mass and thus decreases the hiding power achievable with such particles. Additionally, such particles are single crystals and not in the form of agglomerates of nano primer particles.

The documents Arnab Kanti Giri et al. (doi: 10.1039/C5RA19828C) and Xianbio Wang et al. (doi: 10.1039/C0JM01024C) are related to the technical field of the present application. Yet, the products obtainable using the techniques disclosed in said documents are flakes with rather random shapes without strict control of the geometric form. The document TR2009/07209 seeks solutions for problems related to the production method of microplatelets by agglomeration of the zinc oxide nanoparticles. By virtue of the optical, electrical and chemical properties, the zinc oxide nanoparticles might be used in protective creams, in semiconductor technology and at the defense industry. Said method indicates that the Zn source (zinc oxide) concentration should be 1.55 M for production of a powder in form of microplatelets. Above such limit, deviations from platelet shape and/or unintentional agglomerations occur. On the other hand, considering the production efficiency, working with concentrations at and around 1.55 M may reduce the efficiency in industrial scale production. The platelets obtained with said method have specific surface areas around 23 $m^2/g$. Some applications, however, where the platelets so produced are used require thin and much larger (>30 $m^2/g$) surface area, therefore higher surface covering ability.

The above mentioned production methods available in the prior art enables production of plate-shaped ZnO powders, yet the thickness and geometric forms of such platelets cannot be controlled over any process parameter. Yet, the thickness of the platelet is one of the most important properties that would determine the optical properties (transparency, etc.) in application of the powder. Increase at the surface area per unit mass means that the platelets are getting thinner. Moreover, the shapes of the microplatelets are also extremely important based on the fact that when the platelet shape has the geometry with high covering ability, the same covering ability and performance might be achieved by using lesser amount from the same substance. Therefore, a requirement exists for developing a technique that enables platelet thicknesses that are sufficiently thin enough to ensure transparency (i.e., >30% transmission at 600 nm), that have large surface areas and that allows the platelets to have specific geometric shapes under different production conditions. Accordingly, process conditions should be determined for each admixture containing ZnO system in order to achieve the doped ZnO micro platelets with designed geometry.

Hence, it is desirable to provide a method enabling obtainment of polygonic ZnO platelets having a high median specific surface area, in controlled size and morphology, considering the abovementioned shortcomings.

Primary objective of the present invention is to overcome the above mentioned shortcomings encountered in the prior art.

Another objective of the present invention is provision of a method for obtainment of ZnO microplatelets with controlled agglomeration of nanoparticles so that specific size and morphology is achieved.

A further objective of the present invention is to provide polygonal ZnO microplatelets with high specific surface area.

SUMMARY

The present invention proposes a method for producing polygonic Zinc oxide platelets having a median specific surface area of more than 25 square meters per gram, in controlled size and morphology, the method comprising: preparing a medium including Zn or its compounds at a concentration within the range between 1.55 and 7.75 moles of Zn/L, in a medium suitable to substitute Zn ions by releasing free protons (e.g. hydrogen ions) (e.g. a medium containing hydroxide(s), for instance three hydroxides as in glycerin) thereby forming a complex structure including Zn; agitation of the medium in a vessel at a temperature within the range between 50° C. and 320° C. for a duration up to 10 hours to obtain a suspension; filtering the suspension to obtain a filtrate including solid particles; drying and then calcination of the dried filtrate; wherein the agitation is performed with one or more radial flow impellers so that the Reynolds' number in the vessel is higher than 2500 and lower than 10000. The present invention further proposes a product including such platelets.

BRIEF DESCRIPTION OF THE DRAWINGS

The accompanying drawings are given solely for the purpose of exemplifying the invention whose advantages over prior art were outlined above and will be explained in detail hereinafter.

DETAILED DESCRIPTION OF THE EMBODIMENTS

Figure 1:
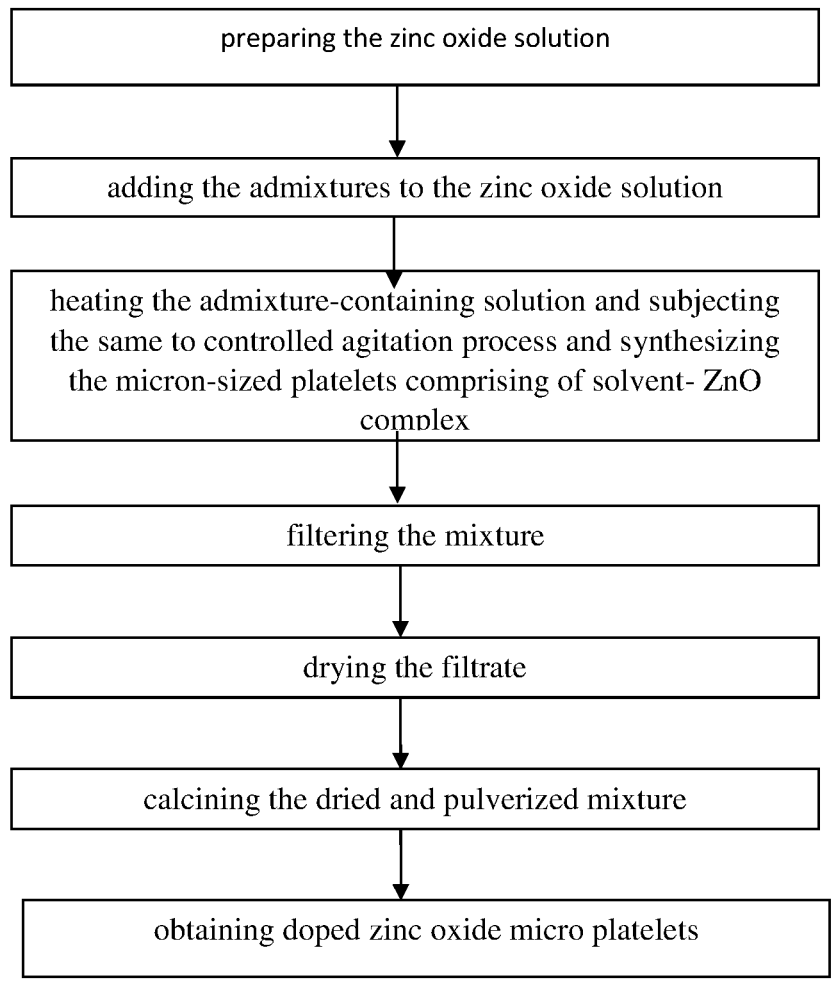
FIG. 1 shows an exemplary flow chart which can be associated with the method according to the present invention.

Referring to the figures summarized above, the present invention proposes a method for producing polygonic Zinc oxide (abbreviated as Zn oxide or ZnO) platelets having a median specific surface area of more than 25 square meters per gram, in controlled size and morphology, the method comprising: preparing a medium including Zn or its compounds at a concentration within the range between 1.55 and 7.75 moles of Zinc per liter, in a medium suitable to substitute Zn ions by releasing free protons (e.g. hydrogen ions) (e.g. a medium containing hydroxides) thereby forming a complex structure including Zn. The method further comprises agitation of the medium in a vessel at a temperature within the range between 50° C. and 320° C. for a duration up to 10 hours to obtain a suspension; filtering the suspension to obtain a filtrate including solid particles; drying the filtrate and calcination of the dried filtrate. In the method according to the present invention, the agitation is performed with one or more radial flow impellers so that the Reynolds' number in the vessel is higher than 2500 and lower than 10000 thereby maintaining below its turbulent flow values, since turbulent flow causes erosion on the platelets and therefore destroys the polygonic platelet geometry.

In a variation of the method according to the present invention, the impelling is performed using a shaft provided with a plurality of radial flow impellers distributed thereon.

The ratio obtained by the diameter of the impeller with respect to the shaft axis at a projection on the shaft, to the diameter of the vessel at the same projection on the shaft can be between 0.3 and 0.4.

Zinc input in preparation of the medium can include one or more material selected from the list consisting of metallic Zinc, Zinc oxide, zinc chloride, zinc acetate, zinc nitrate, zinc sulphate, zinc bromide, zinc carbonate, zinc oxalate, diethyl zinc, zinc chromate, zinc arsenate, zinc arsenide, zinc phosphate, zincate, zinc molybdate, zinc cyanide, zinc iodide, zinc fluoride, zinc carbide, zinc selenite, zinc sulphur, zinc hydride, zinc antimonite, zinc arsenide, zinc phosphide and zinc nitride. In particular, the Zinc input in preparation of the medium can include ZnO.

To obtain doped zinc oxide micro platelets, materials that contain metallic elements/ions that can modify the properties of ZnO by penetrating into the ZnO structure can be included in the medium. Accordingly the medium can comprise one of the further metals selected from the list consisting of Aluminium (Al), Gallium (Ga), Silver (Ag), Indium (In), Iron (Fe) and Cobalt (Co) as an admixture, the further metal being in its elementary form, or in form of one or more oxides and/or one or more salts thereof, wherein the initial concentration of the admixture in the medium is within the range between 0.01% and 20% (mol/mol) of with respect to the Zn.

The medium can include one or more of the compounds selected from the list consisting of glycerin, glycolates, ethylene glycol, 1,3 propanediol, tri-hydroxy benzene, tri-hydroxy benzoic acid, tri-hydroxy butane and tri-hydroxy pentane. In particular, said compound can be glycerin thereby being more suitable in terms of labor safety.

The agitation can be performed at a temperature within the range between 200° C. and 280° C., particularly between 220° C. and 270° C. for provision of sufficient rate in agglomeration whilst maintaining the reaction temperature in a moderate extent. With these temperatures, satisfying results are observed in terms of size and geometry, with reaction times of about 1 hour. Accordingly, the duration of the agitation can be within the range between 45 and 75 minutes, particularly between 55 and 65 minutes.

The filtering can be performed using a further medium having a lower polarity relative to the medium used in the preparation of the medium. The further medium can particularly be isopropyl alcohol because of its low price and of being benign in terms of labor safety.

The drying of the filtrate can be performed at a temperature below 65° C. Such mild conditions serve for preventing the medium (or the further medium if applicable) from catching fire in the drying step.

The calcination can be performed at a temperature within the range between 200° C. and 700° C., particularly between 300° C. and 500° C., more particularly between 325° C. and 425° C. These narrower ranges provide acceptable extents of calcination in acceptable durations with optimal levels of energy consumption.

EXAMPLES

The below examples represent several experimental results obtained in a laboratory scale setup, and it is aimed solely to provide a closer introduction of the inventive concept, rather than limiting the scope of protection sought which is defined by the claims.

The solvo-thermal technique for obtaining the experimental results includes the following steps;
i. preparation of a medium including Zinc or its compounds (ZnO was used in the experiments presented herein) at a concentration within the range between 1.55 and 7.75 moles of Zinc per liter, in a medium suitable to substitute Zn ions by releasing free protons thereby forming a complex structure including Zn (glycerin was used as an exemplary medium),
ii. optionally adding admixtures to the medium in case where the end product of the solvo-thermal process is aimed to be doped micro-platelets,
iii. agitation of the medium in a vessel at a temperature within the range between 50° C. and 320° C. for a duration up to 10 hours to obtain a suspension, thereby synthesizing a solvent-ZnO complex; the agitation being performed using a radial flow impeller and the agitation speed is accorded so that the Reynolds' number in the vessel is maintained higher than 2500 and lower than 10000 throughout the complex formation;
iv. filtering the mixture, optionally using isopropyl alcohol as further medium,
v. drying the filtrate,
vi. calcination of the dried filtrate thereby obtaining ZnO micro platelets doped zinc oxide micro platelets, (the platelets obtained being doped in case where admixtures were employed).

In a first run according to the method; a ZnO nanoparticles were added into a medium comprising glycerin so that the medium includes 5.17 M (i.e. mol/L) of ZnO. The medium is then heated to a temperature of 260° C. (+/−10° C.) under continuous agitation at a speed of 225-900 rpm so that a calculated Reynold's number in an extent of 2500-10000 is maintained in the medium. The duration where the medium is kept over 50° C. under continuous agitation was 1 hour. In a preferred application, the duration where the medium is to be kept at the temperature of 260° C. (+/−10° C.) under continuous agitation is 1 hour. A SEM photograph of ZnO micro particles obtained are shown in the FIG. 6.

Figure 8:
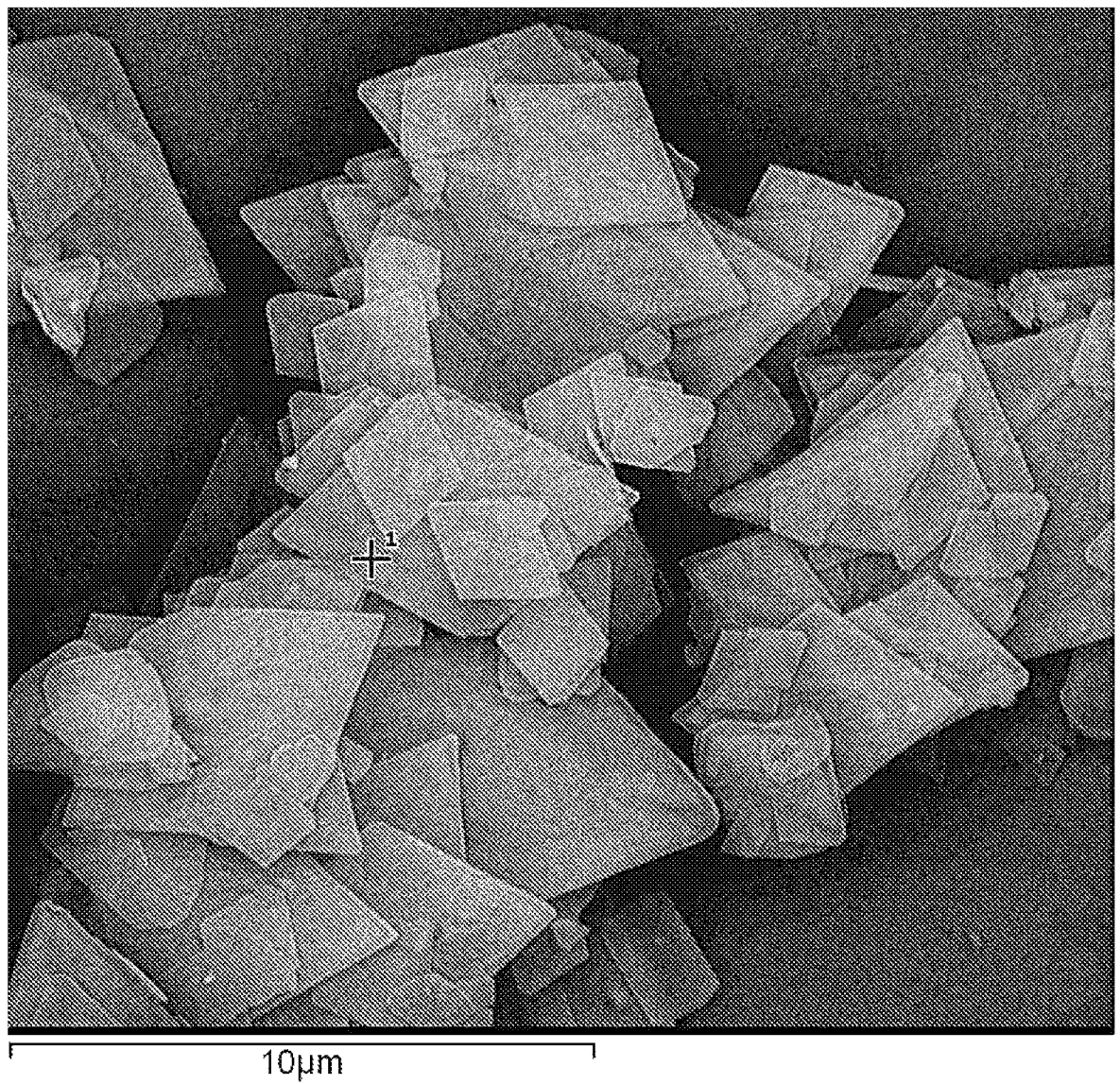
FIG. 8 shows an SEM image of tetragonal ZnO micro platelets having a specific surface area of 33 m²/g, obtained using the method according to the present invention, with admixing 1% (mol/mol) of Al when compared to Zinc.

A second run was also conducted, and differed from the first run in: admixtion of 1% (mol/mol) of Aluminium containing nanoparticles with respect to the amount of the Zn; the agitation speed being kept between 500 and 900 rpm; and thereby obtaining tetragonal ZnO microplatelets doped with Al in a concentration of 1 mole % with respect to the amount of the ZnO (which is essentially equal to the amount of the Zn in moles), SEM image of which being shown in FIG. 8. Said Aluminium containing nanoparticles are selected from aluminium salts or other Al-compounds including aluminium chloride, aluminium nitrate, aluminium acetate, aluminium hydroxide and aluminium oxides.

Figure 9:
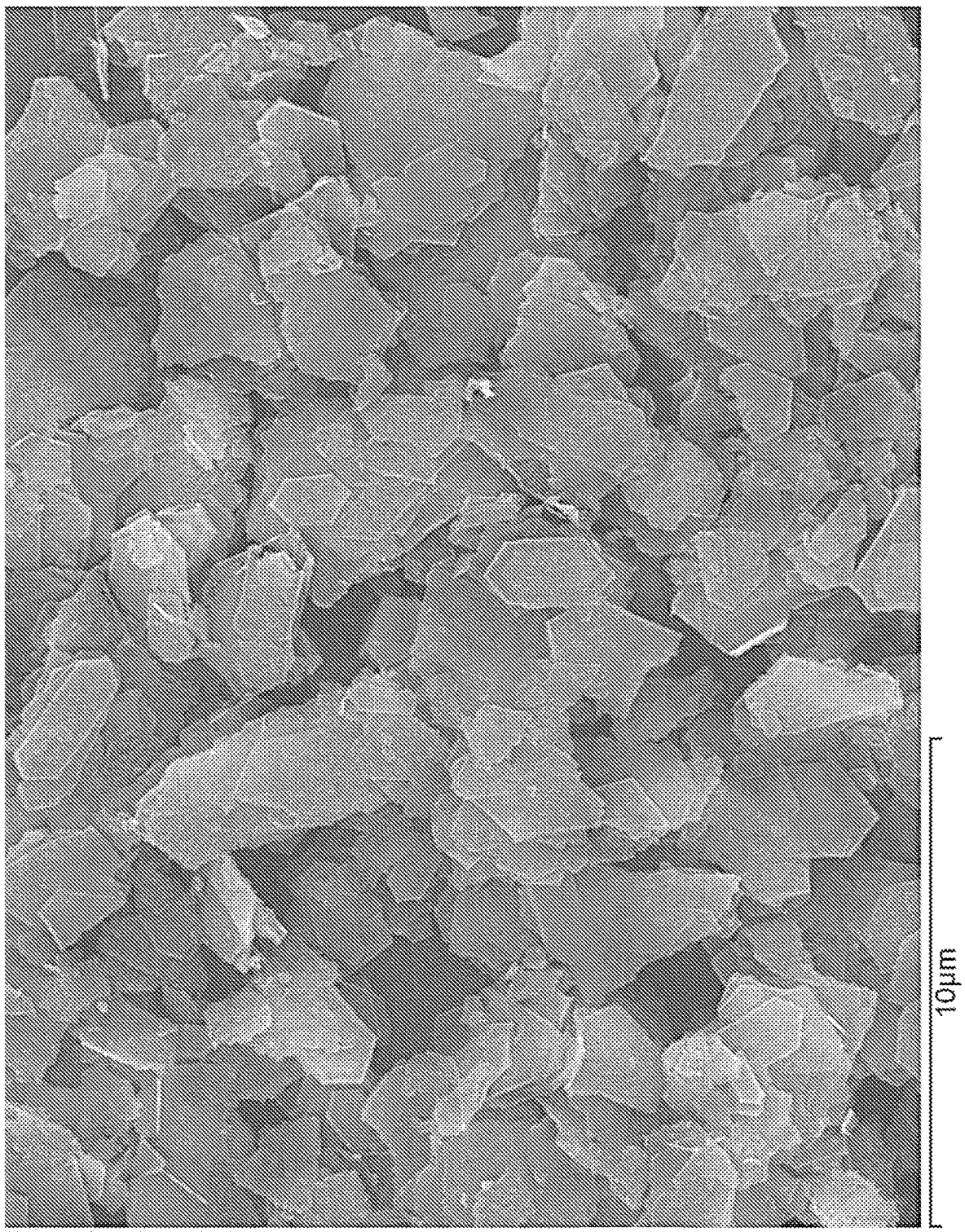
FIG. 9 shows an SEM image of hexagonal ZnO micro platelets having a specific surface area of 30 m²/g, obtained using the method according to the present invention, with admixing 1% (mol/mol) of Ga when compared to Zinc.

A third run was also conducted, and differed from the first run in: admixtion of 1% of Gallium containing nanoparticles into the medium with respect to the amount of the Zn; the agitation speed being kept between 300 and 1000 rpm; and thereby obtaining hexagonal ZnO microplatelets doped with Ga in a concentration of 1% (mol/mol) with respect to the amount of the Zn, SEM image of which being shown in FIG. 9. Said Gallium containing nanoparticles are selected from gallium salts or other Ga-compounds including gallium chloride, gallium nitrate, gallium acetate, gallium hydroxide and gallium oxides.

Figure 10:
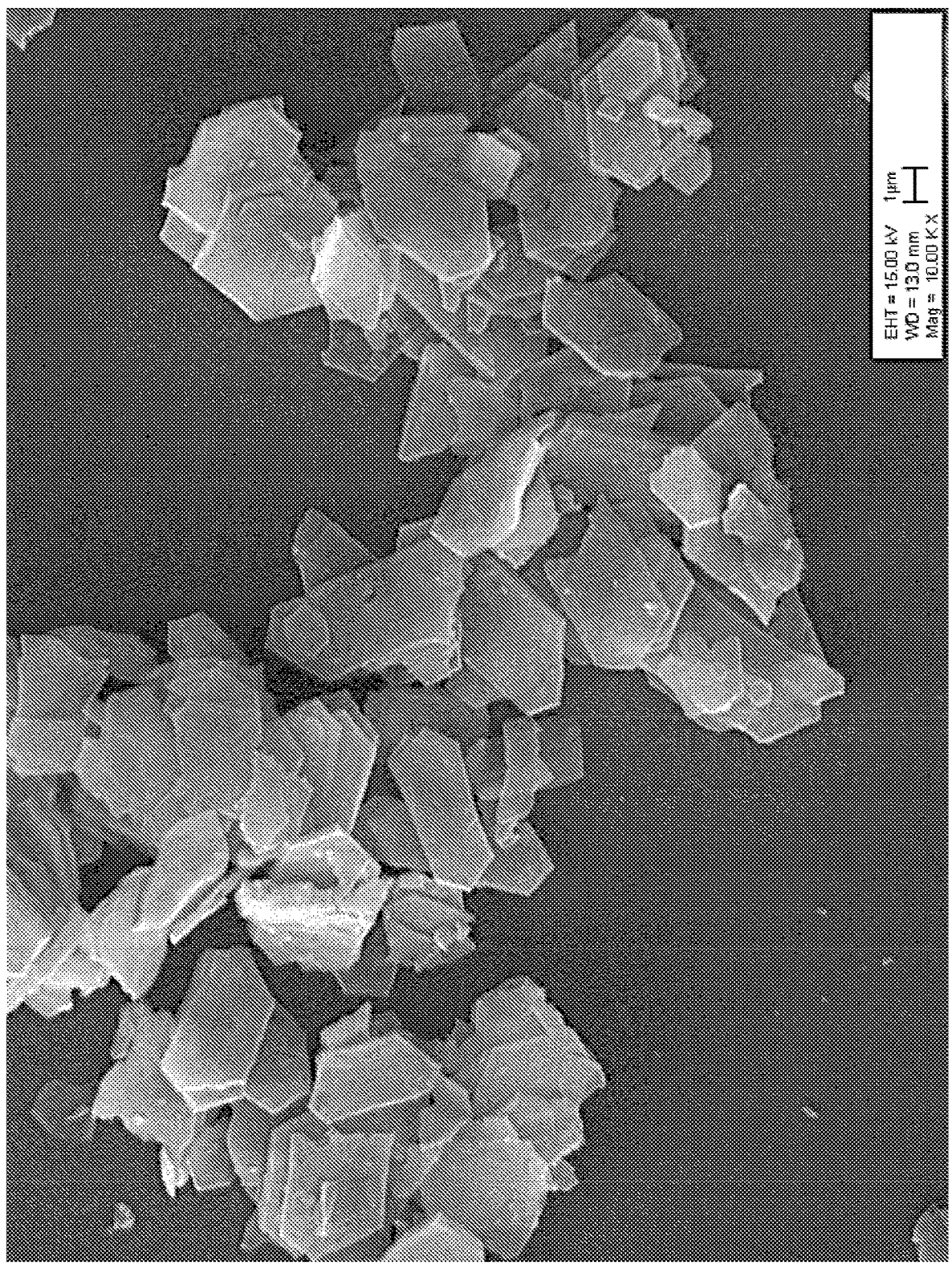
FIG. 10 shows an SEM image of hexagonal ZnO micro platelets having a specific surface area of 41 m²/g, obtained using the method according to the present invention, with admixing 1% (mol/mol) of Ag when compared to Zinc.

A fourth run was also conducted, and differed from the first run in: admixtion of 1% (mol/mol) of Silver containing nanoparticles (in this case, silver nitrate) with respect to the amount of Zn; the agitation speed being kept between 200 and 900 rpm; and thereby obtaining pentagonal ZnO microplatelets doped with Ag in a concentration of 1% (mol/mol) with respect to the amount of the Zn, SEM image of which being shown in FIG. 10. Said Silver containing nanoparticles are selected from silver salts or other Ag-compounds including silver chloride, silver nitrate, silver acetate, silver hydroxide and silver oxides.

Figure 11:
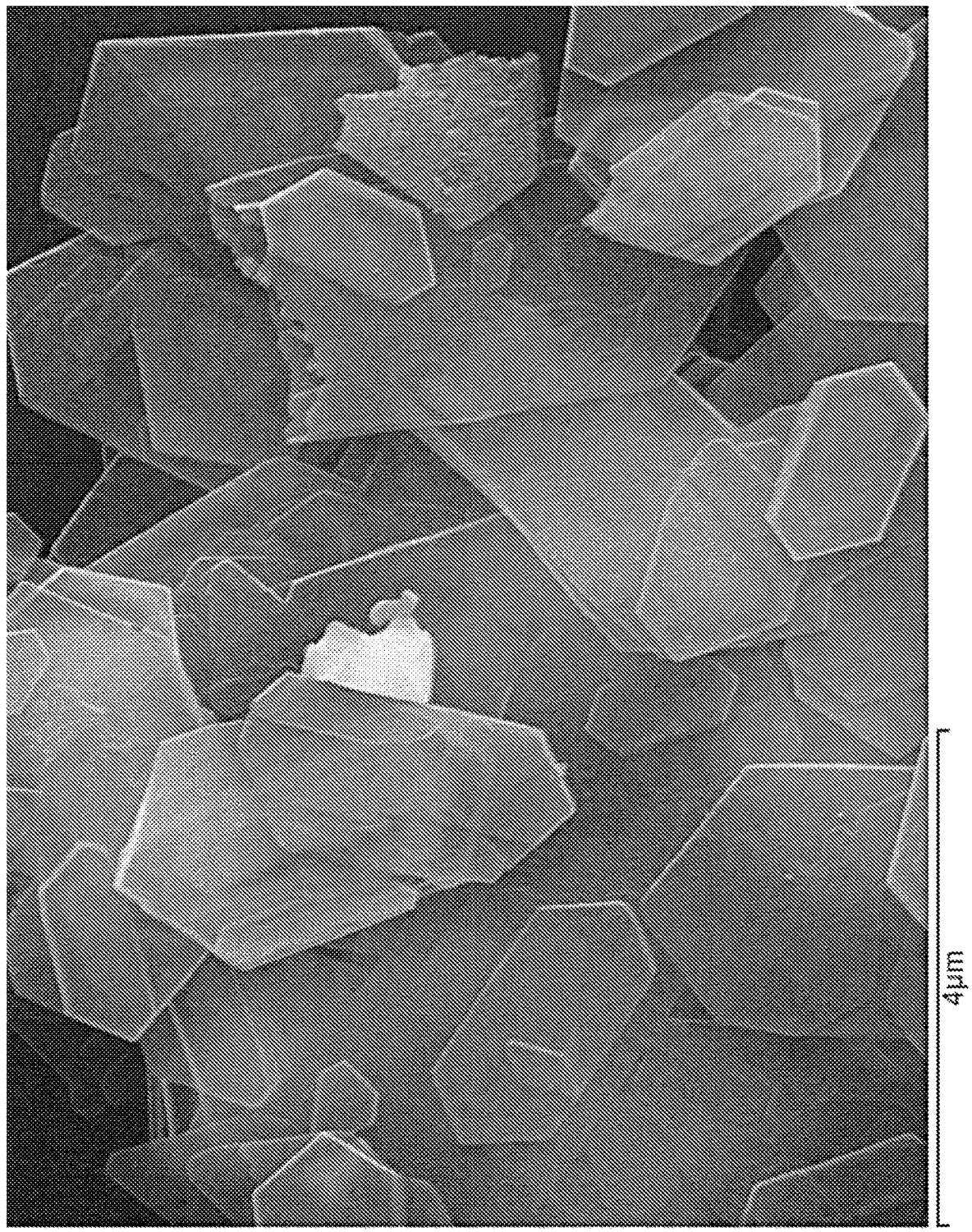
FIG. 11 shows an SEM image of hexagonal ZnO micro platelets having a specific surface area of 29 m²/g which is highly favorable by being greater than 25 m²/g, obtained using the method according to the present invention, with admixing 1% (mol/mol) of In when compared to Zinc.

A fifth run was also conducted, and differed from the first run in: admixtion of 1% (mol/mol) of Indium containing nanoparticles (in this case, indium oxide) with respect to the amount of Zn; the agitation speed being kept between 500 and 1000 rpm; and thereby obtaining hexagonal ZnO microplatelets doped with In in a concentration of 1% (mol/mol) with respect to the amount of the Zn, SEM image of which being shown in FIG. 11. Said Indium containing nanoparticles are selected from Indium salts or other In-compounds including indium chloride, indium nitrate, indium acetate, indium hydroxide and indium oxides.

Figure 12:
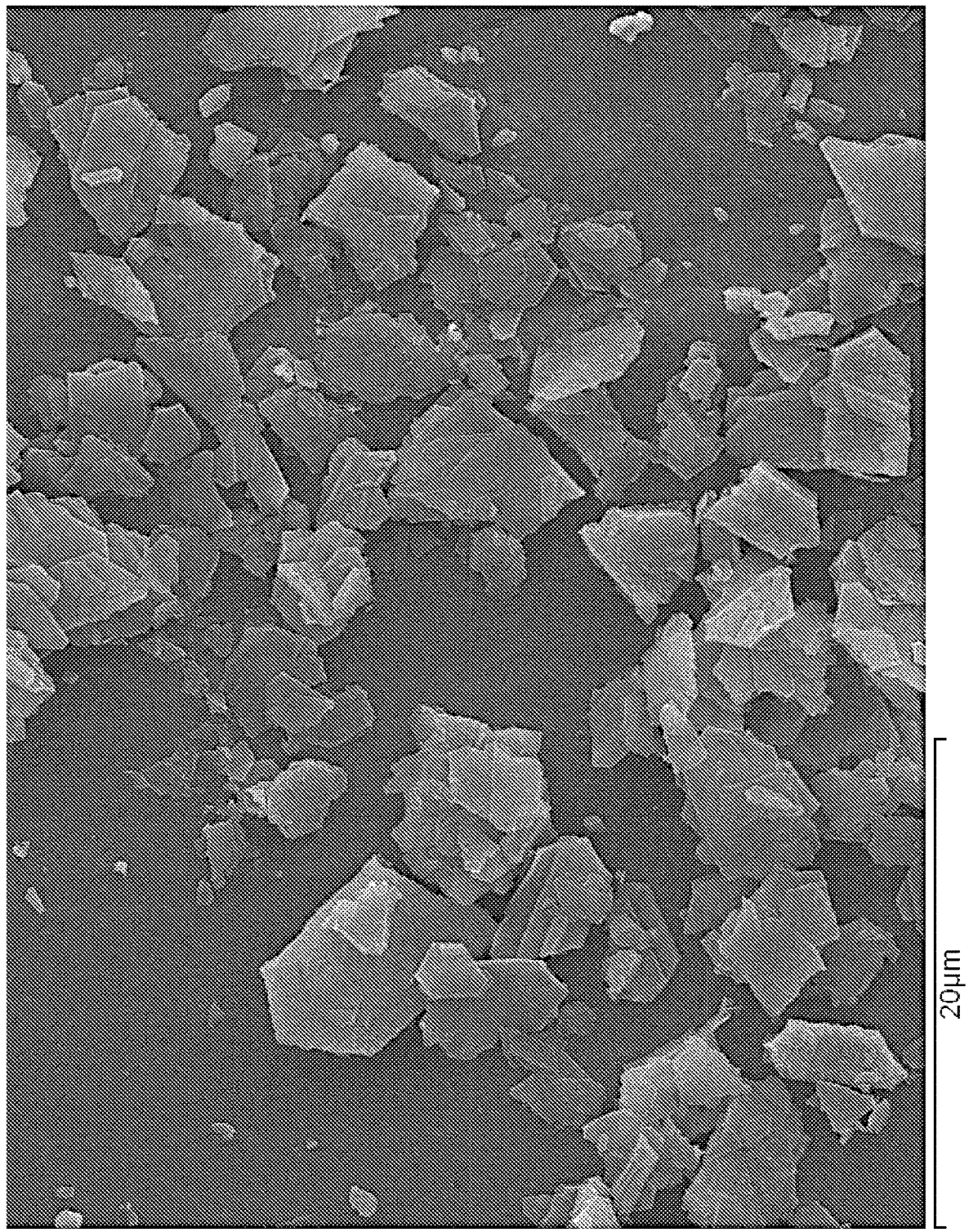
FIG. 12 shows an SEM image of hexagonal ZnO micro platelets having a specific surface area of 33 m²/g, obtained using the method according to the present invention, with admixing 1% (mol/mol) of Fe when compared to Zinc.

A sixth run was also conducted, and differed from the first run in: admixtion of 1% (mol/mol) of Iron containing nanoparticles (in this case, iron chloride) with respect to the amount of Zn; the agitation speed being kept between 100 and 600 rpm; and thereby obtaining hexagonal ZnO microplatelets doped with Fe in a concentration of 1% (mol/mol) with respect to the amount of the Zn, SEM image of which being shown in FIG. 12. Said iron containing nanoparticles are selected from iron salts or other Fe-compounds including iron chloride, iron nitrate, iron acetate, iron hydroxide and iron oxides.

Figure 13:
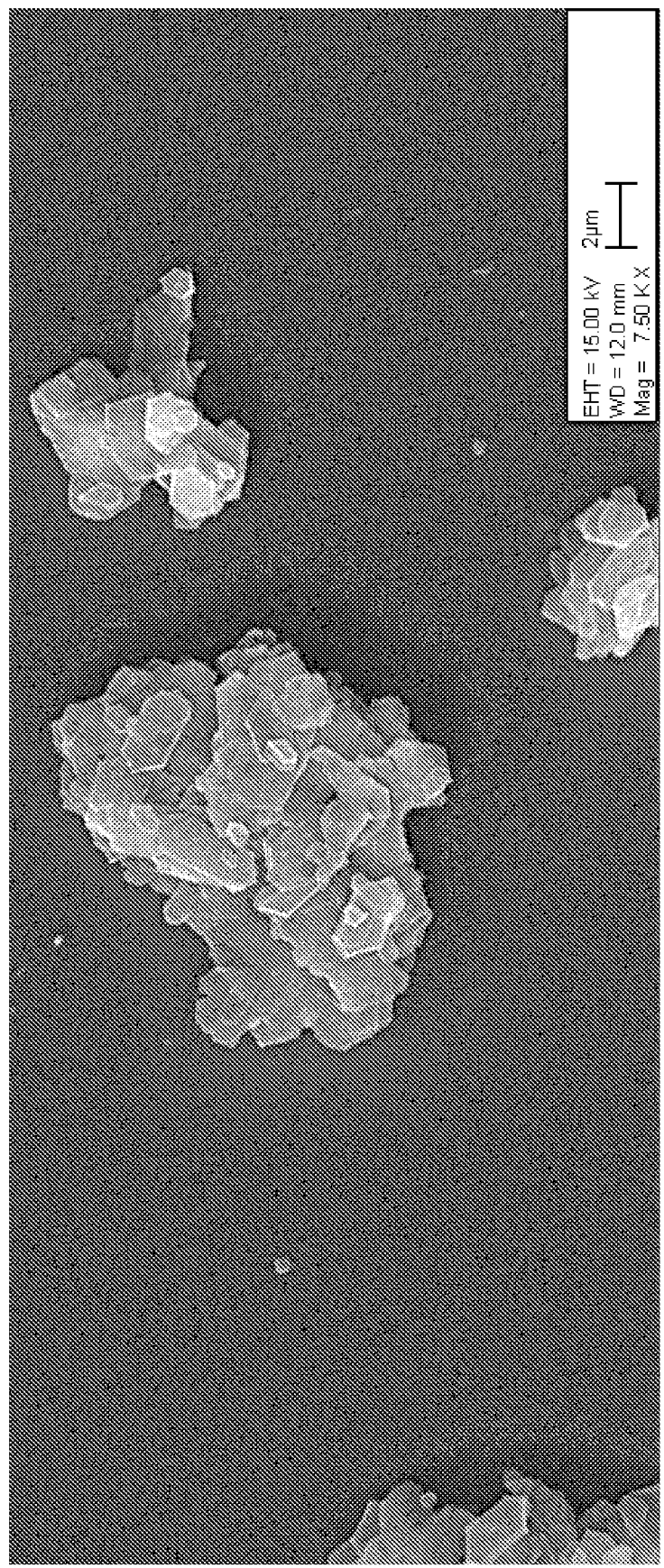
FIG. 13 shows an SEM image of hexagonal ZnO micro platelets having a specific surface area of 34 m²/g, obtained using the method according to the present invention, with admixing 1% (mol/mol) of Co when compared to Zinc.
Figure 14:
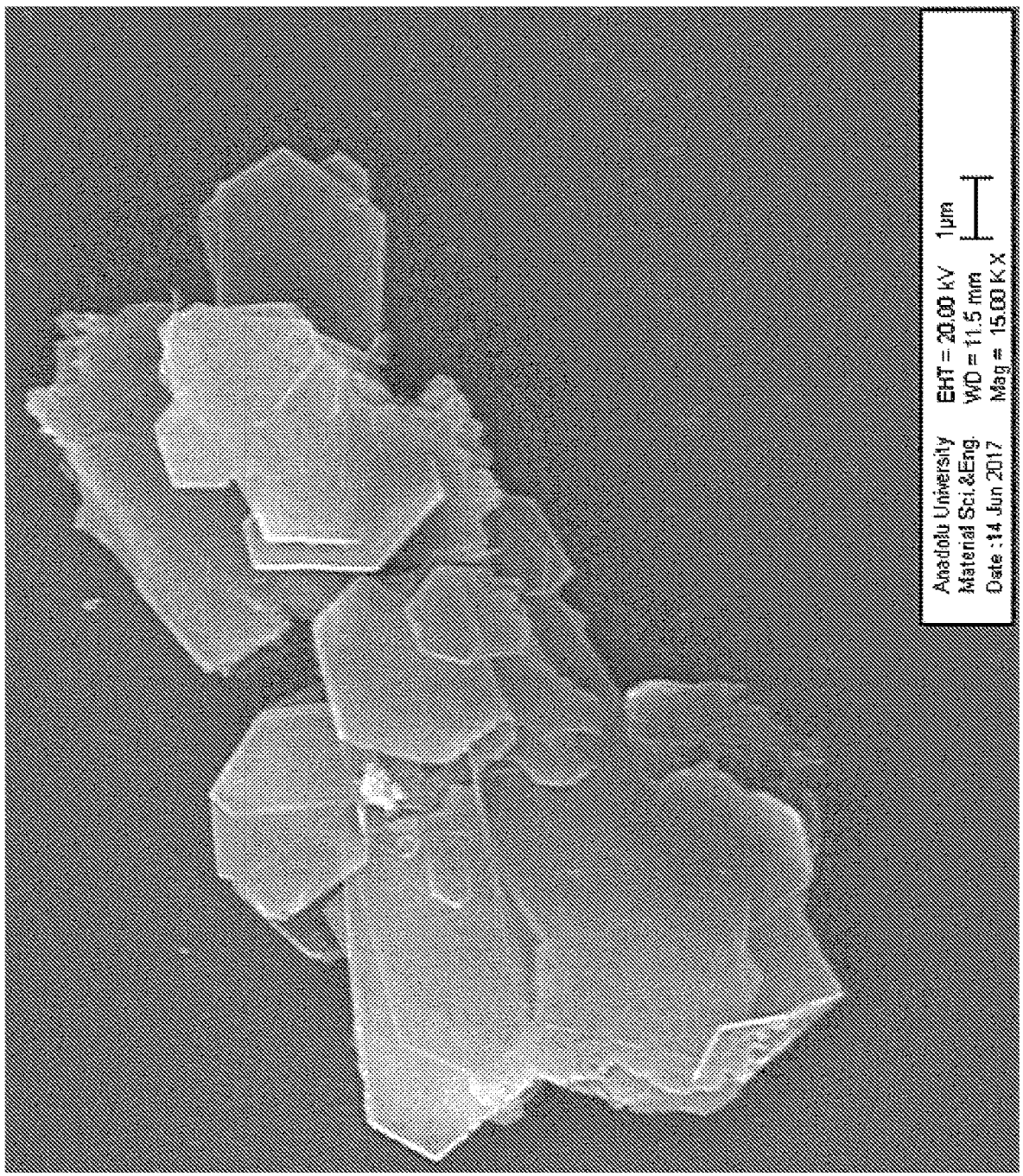
FIG. 14 shows an SEM image of ZnO hexagonal micro platelets having a specific surface area of 30 m2/g obtained using the method according to the present invention, with admixing of 2% (mol/mol) of Ti when compared to Zn. The solution concentration was 5.17 M.
Figure 15:
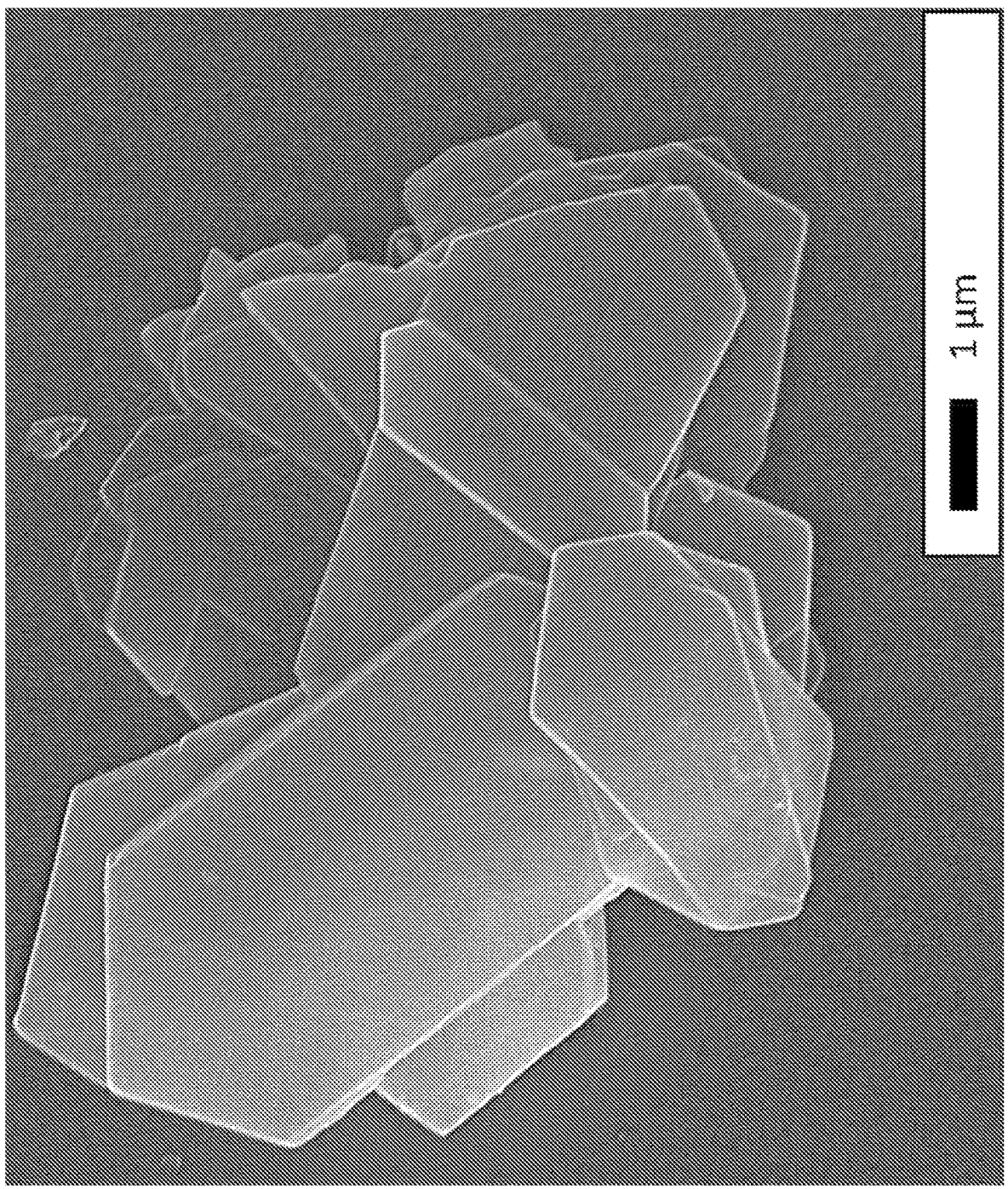
FIG. 15 shows another SEM image of the ZnO platelets obtained with the method according to the present invention.
Figure 16:
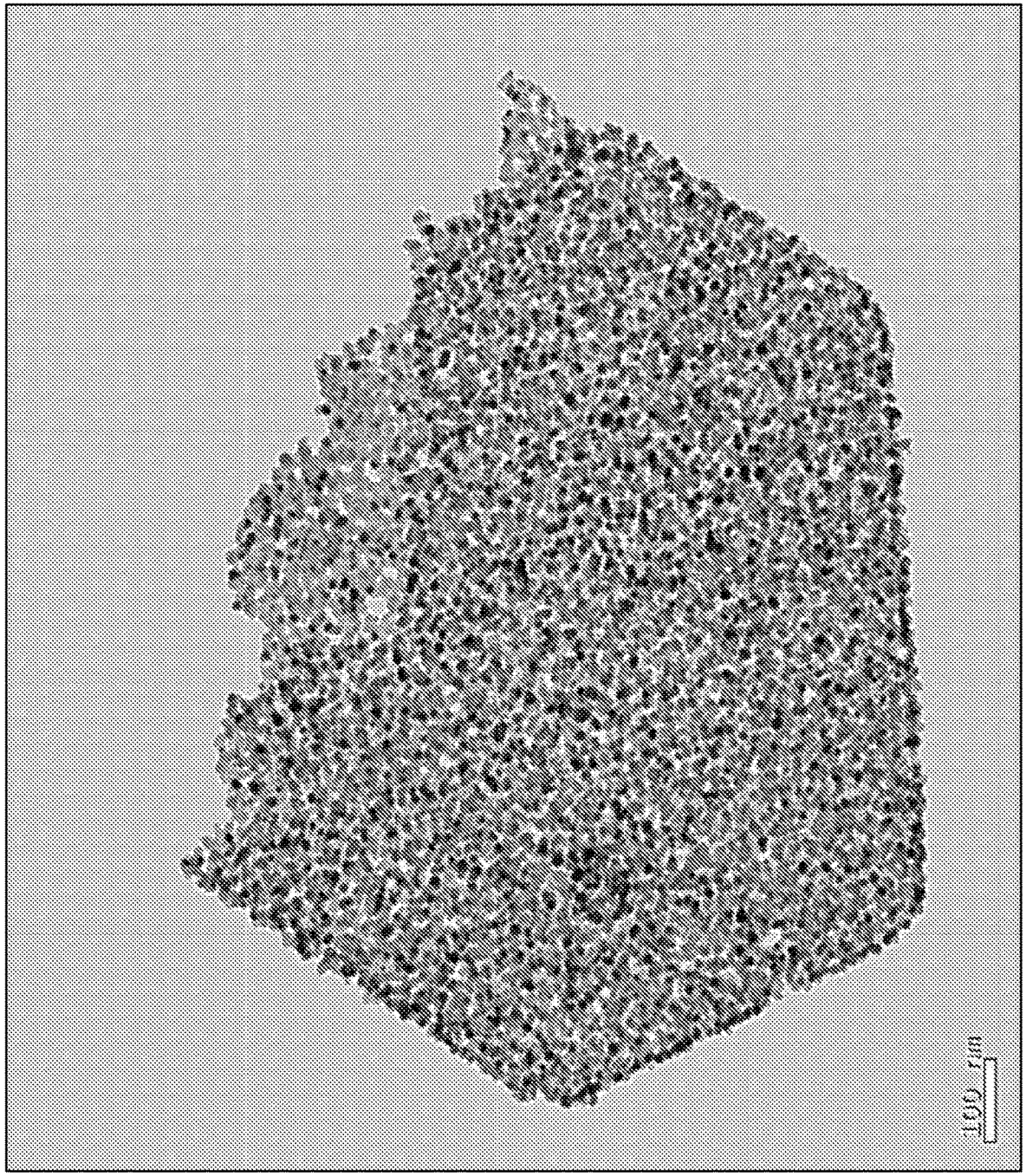
FIG. 16 shows a Transmission Electron Microscope (TEM) image of the ZnO particles, produced by the method according to the present invention.
Figure 17:
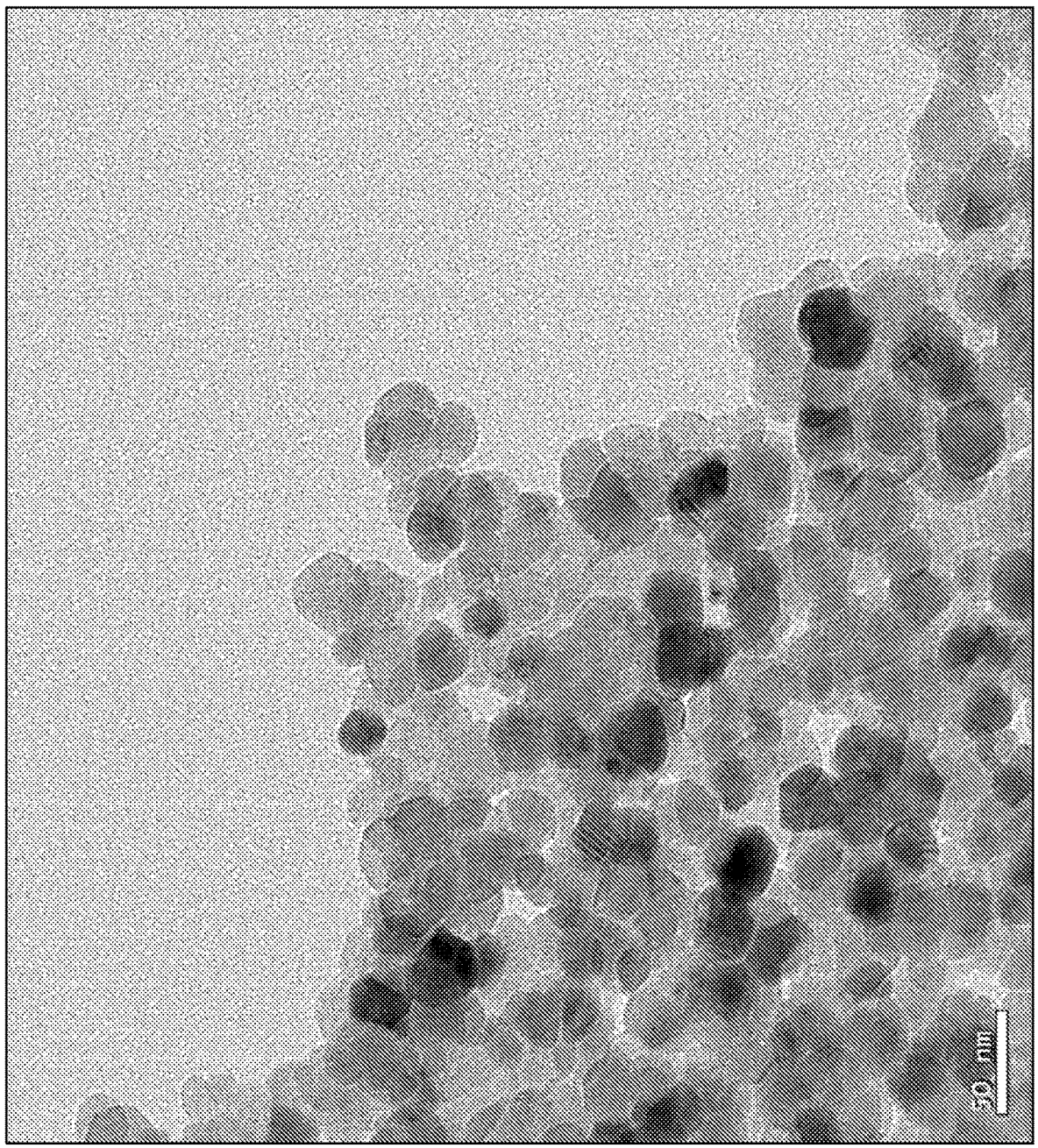
FIG. 17 shows another TEM image of the ZnO particles, produced by the method according to the present invention.
Figure 18:
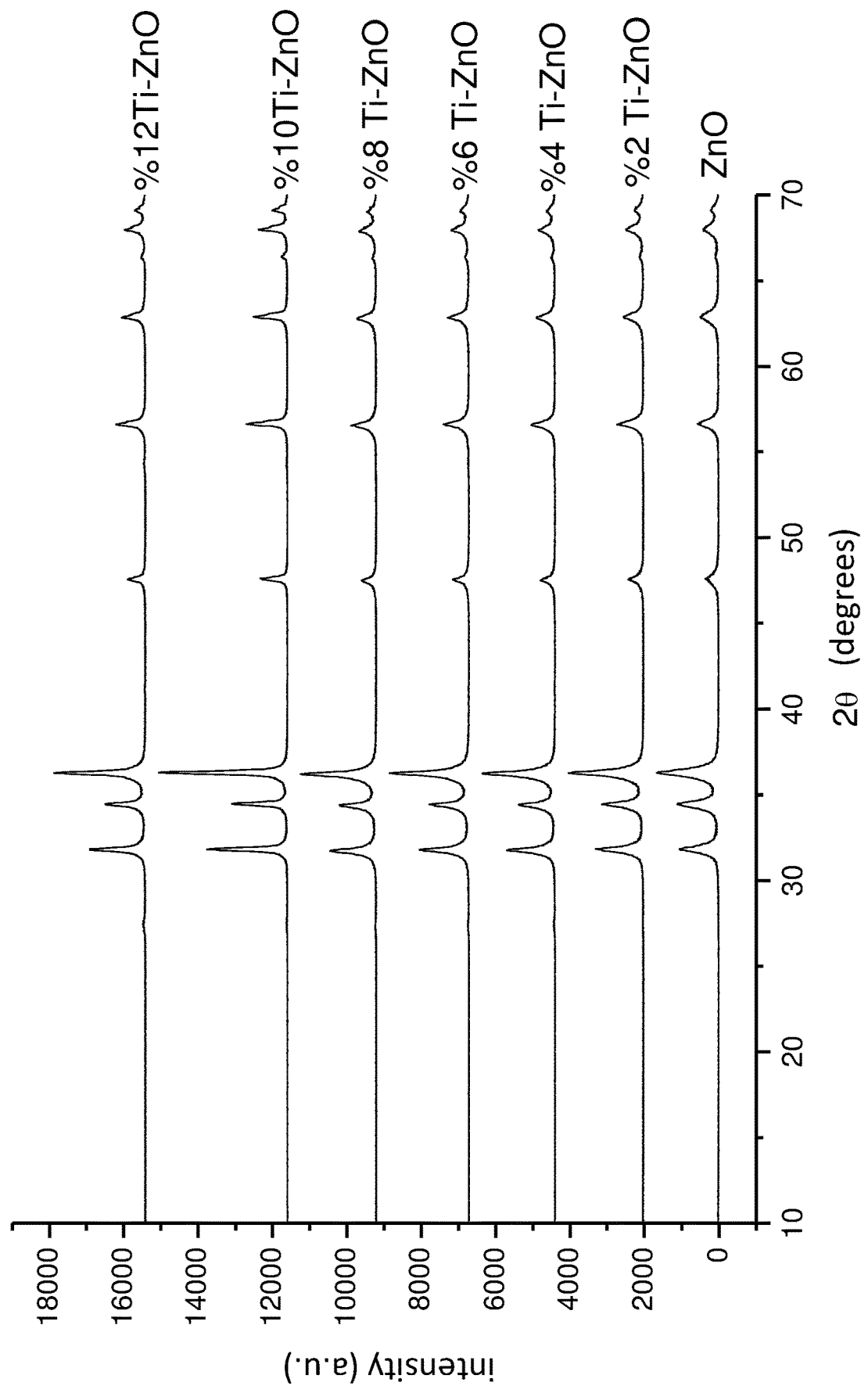
FIG. 18 shows comparative XRD patterns of the ZnO micro platelets with Ti admixtures at variable mole fractions manufactured with the method according to the invention.
Figure 19:
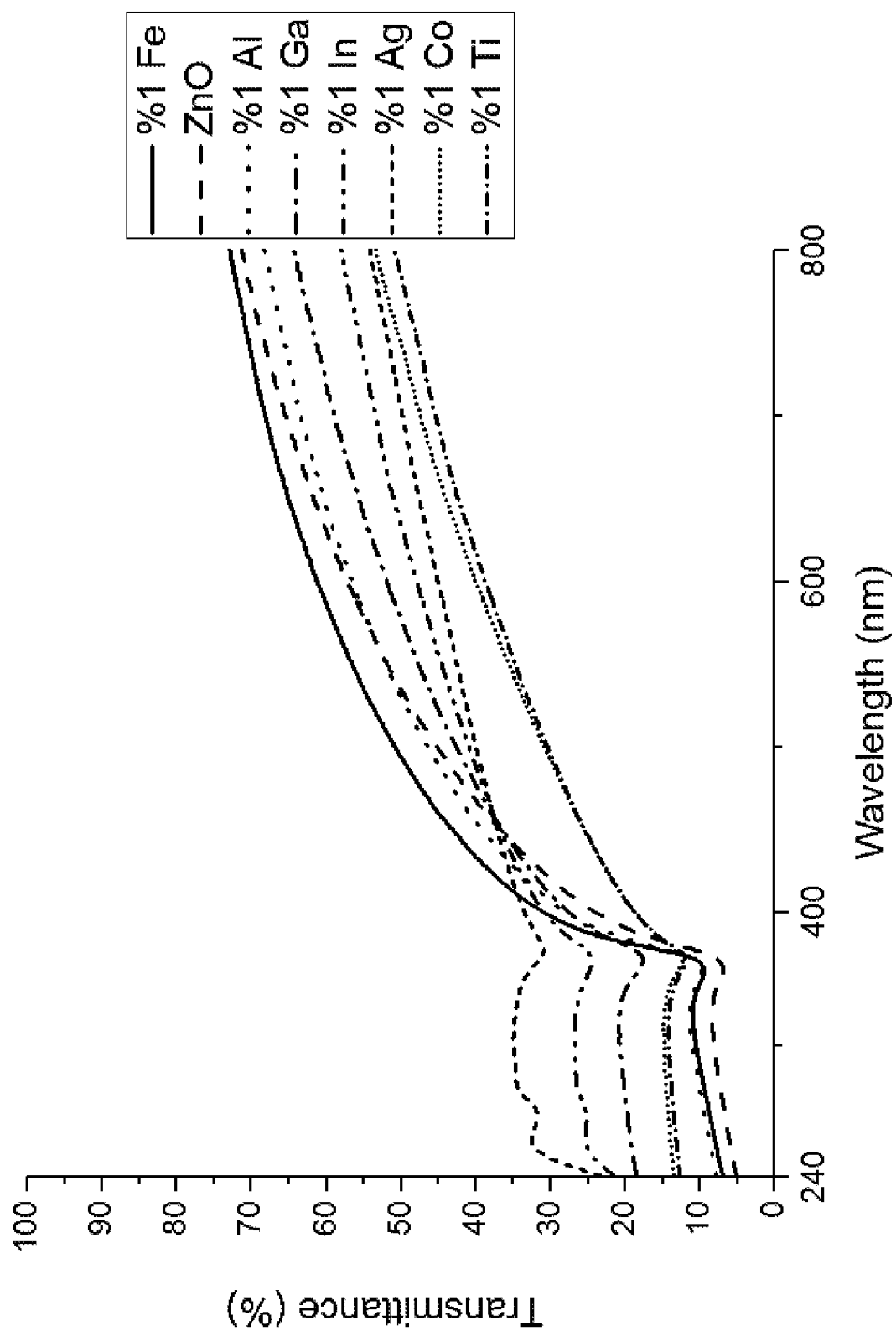
FIG. 19 shows the UV-Vis Spectra of ZnO and doped ZnO platelets described in the respective examples in the present description.

A seventh run was also conducted, and differed from the first run in: admixtion of 1% (mol/mol) of Cobalt nanoparticles (in this case, cobalt oxide) with respect to the amount of the Zn; the agitation speed being kept between 100 and 600 rpm; and thereby obtaining hexagonal ZnO microplatelets doped with Co in a concentration of % (mol/mol) with respect to the amount of the Zn, SEM image of which being shown in FIG. 13. Said cobalt containing nanoparticles are selected from cobalt salts or other Co-compounds including cobalt chloride, cobalt nitrate, cobalt acetate, cobalt hydroxide and cobalt oxides.

In the experimental runs described above; the lower limits of mixing speeds represent the mixing speeds at which particles of solvent-ZnO complex are assumed to start to form polygonic micro platelets under hydrodynamic forces exerted thereonto; and the upper limits of mixing speeds represent the mixing speeds where the microplatelets start to deteriorate to transform back into agglomerated and or irregular forms of submicron particles.

Upon synthesizing of the above described polygonic micro platelets essentially constituted from solvent-ZnO complex, the reaction mixtures were filtered and using isopropanol as the optional further medium. The filtrate is then dried in a drying oven which was maintained at approximately 50° C. The powder obtained upon the drying step is then calcined at a temperature of 350+/−10° C., thereby obtaining polygonic zinc oxide micro platelets.

Analysis results indicated that the specific surface area of the micro platelets is larger than 25 and even 30 m2/g, which in turn is advantageous in terms of surface covering capability. Moreover, the micro platelets are thin enough to ensure transparency can be achieved by virtue of the production method incorporating agitation control. The platelets in the powder obtained with the method according to the present invention show identical properties with the nanometer sized zinc oxide particles in terms of their chemical, biological and optical behavior; yet they cannot penetrate through the skin by virtue of being in micron scale, hereby preventing the carcinogenic effect that arise when zinc oxide mixes into blood.

The micro platelets obtained with the method according to the present invention have the potential to find use in a great range of applications due to their optical and chemical properties and geometric shapes. They can particularly be employed in cosmetic products, which are to be brought into direct contact with the human skin, e.g. moisturizers, sun creams, baby powder. In addition to these, such structures can also find use in semi-conductor technology, antimicrobial coating practices, water treatment systems and in the defense industry for defeating the warfare agents.

Figure 2:
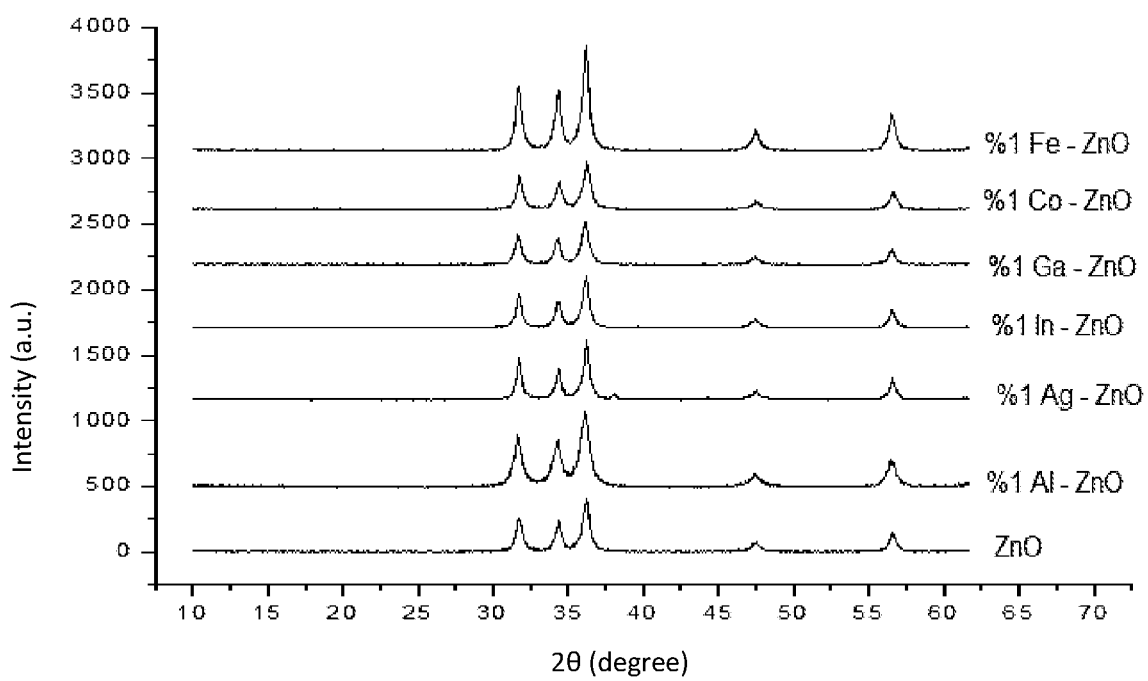
FIG. 2 shows comparative XRD patterns of the pure ZnO micro platelets with aluminum (Al), iron (Fe), cobalt (Co), silver (Ag), gallium (Ga) and indium (In) admixtures, which constitute 1% (mol/mol) of the platelets with respect to the mole concentration of the Zinc.

The admixtures used in the method can also be customized depending on the potential fields of use. Al, Ga and/or In as admixture, the electrical conductivity of the micro platelets can be improved. Ag as admixture provides antimicrobial properties to the micro platelets. Fe, and/or Co as admixtures, on the other hand, introduces photo-catalytic properties, and provides magnetic properties. Accordingly, the medium can comprise one of the further metals selected from the list consisting of Aluminium, Gallium, Silver, Indium, Iron and Cobalt as an admixture, the further metal being in its elementary form, or in form of one or more oxides and/or one or more salts thereof, and the initial concentration of the admixture in the medium can be within the range between 0.01 and 20% (mol/mol) of with respect to the Zn The FIG. 2 shows the peaks of both doped and pure ZnO microplatelets obtained in the above mentioned runs performed using the method according to the present invention. The shift of the peak positions towards right or left at the doped systems compared to pure ZnO directs to the fact that the admixtures enter into the ZnO structure and alter the interplanar distances. Another conclusion that can be drawn from the XRD patterns in the figure is that the peaks are broad, which is an indication of the fact that ZnO micro platelets are formed through agglomeration of ZnO nanoparticles.

Figure 3:
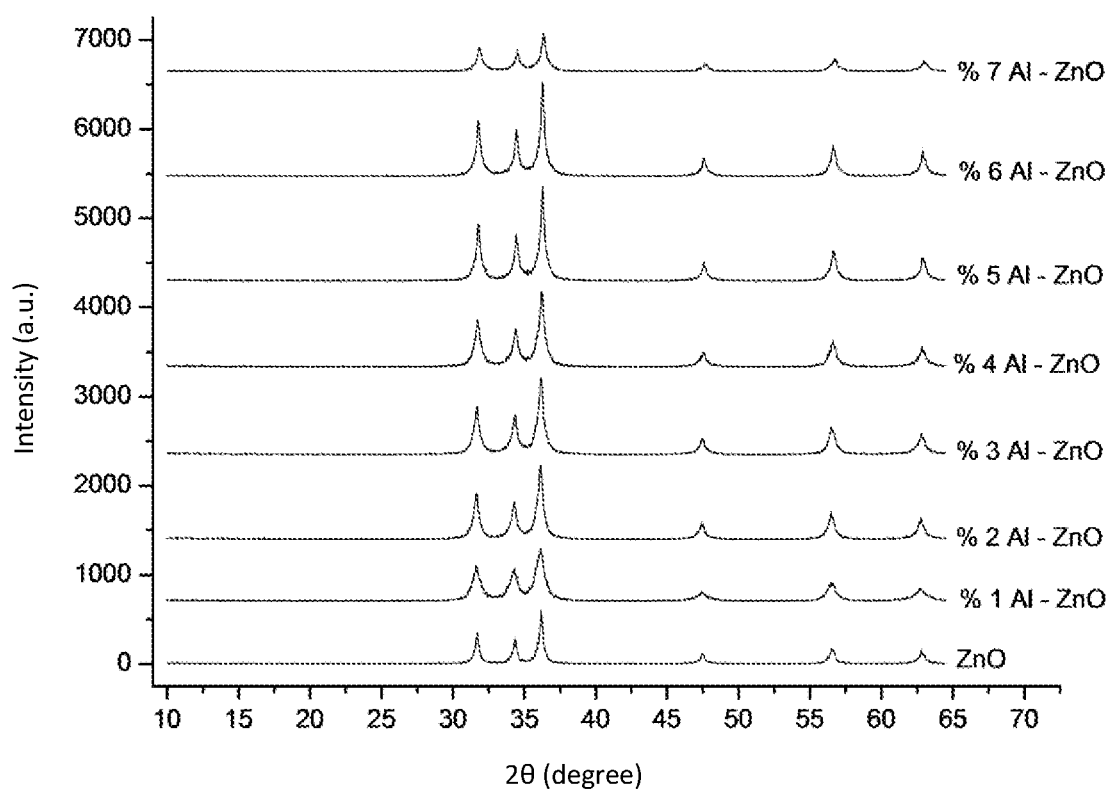
FIG. 3 shows comparative XRD patterns of the ZnO micro platelets with Al admixture at variable mole rates manufactured with the method according to the invention.

The fact that the peaks of ZnO has a tendency to shift towards right with the increased quantity of Al admixture, as illustrated in FIG. 3, indicates that the Al admixture enters into ZnO structures and, as the Al element is smaller than the Zn element it replaces in the structure, reduces the interplanar distance of the ZnO crystal structure. FIG. 3 further proves that the primary particles are nano-sized by virtue of the broad peaks observed, as is the case mentioned above.

Figure 4:
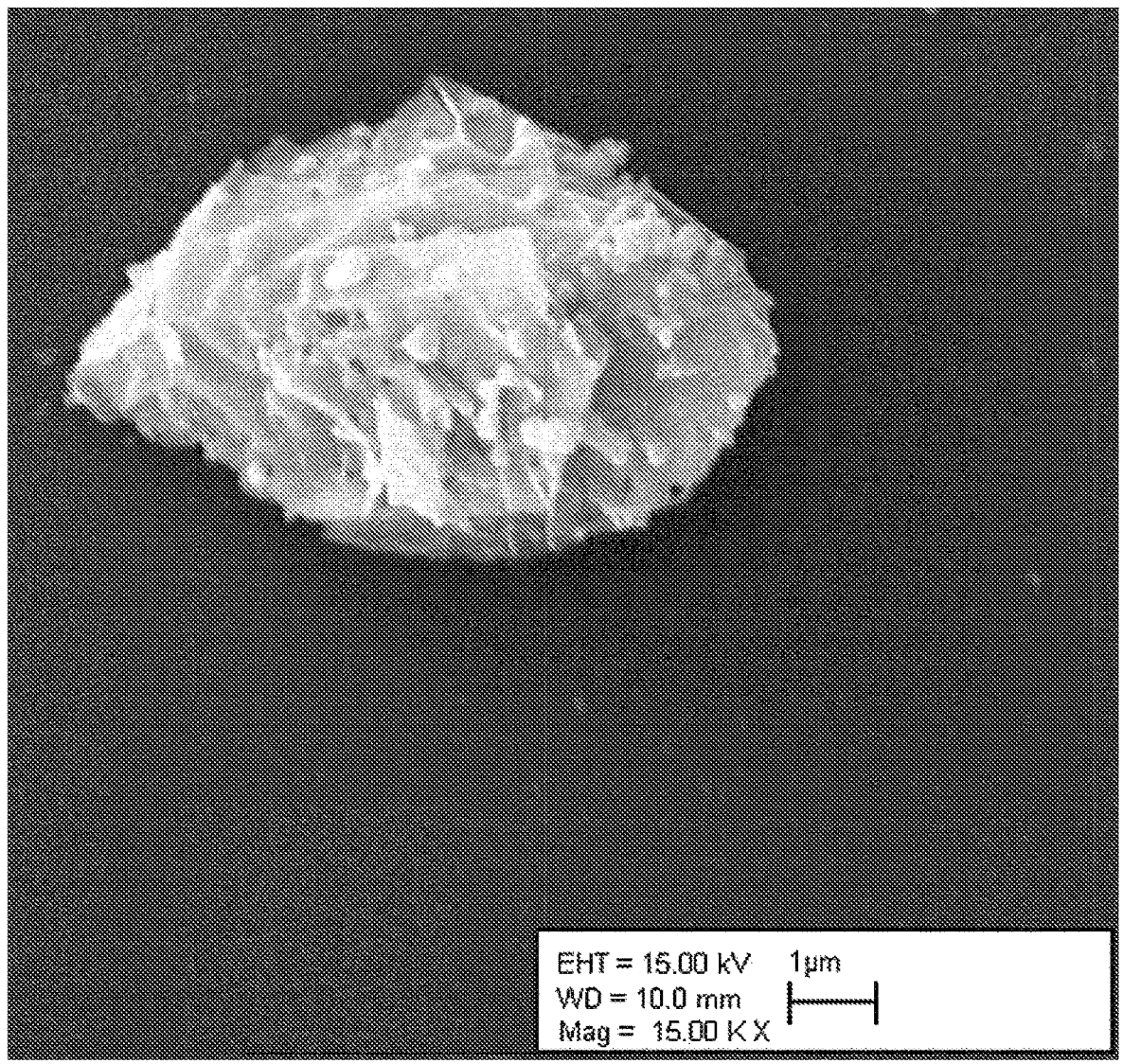
FIG. 4 shows an SEM image of ZnO micro particles obtained from the solution at a concentration of 5.17 M containing admixture-free nano-sized ZnO particles without agitation.
Figure 5:
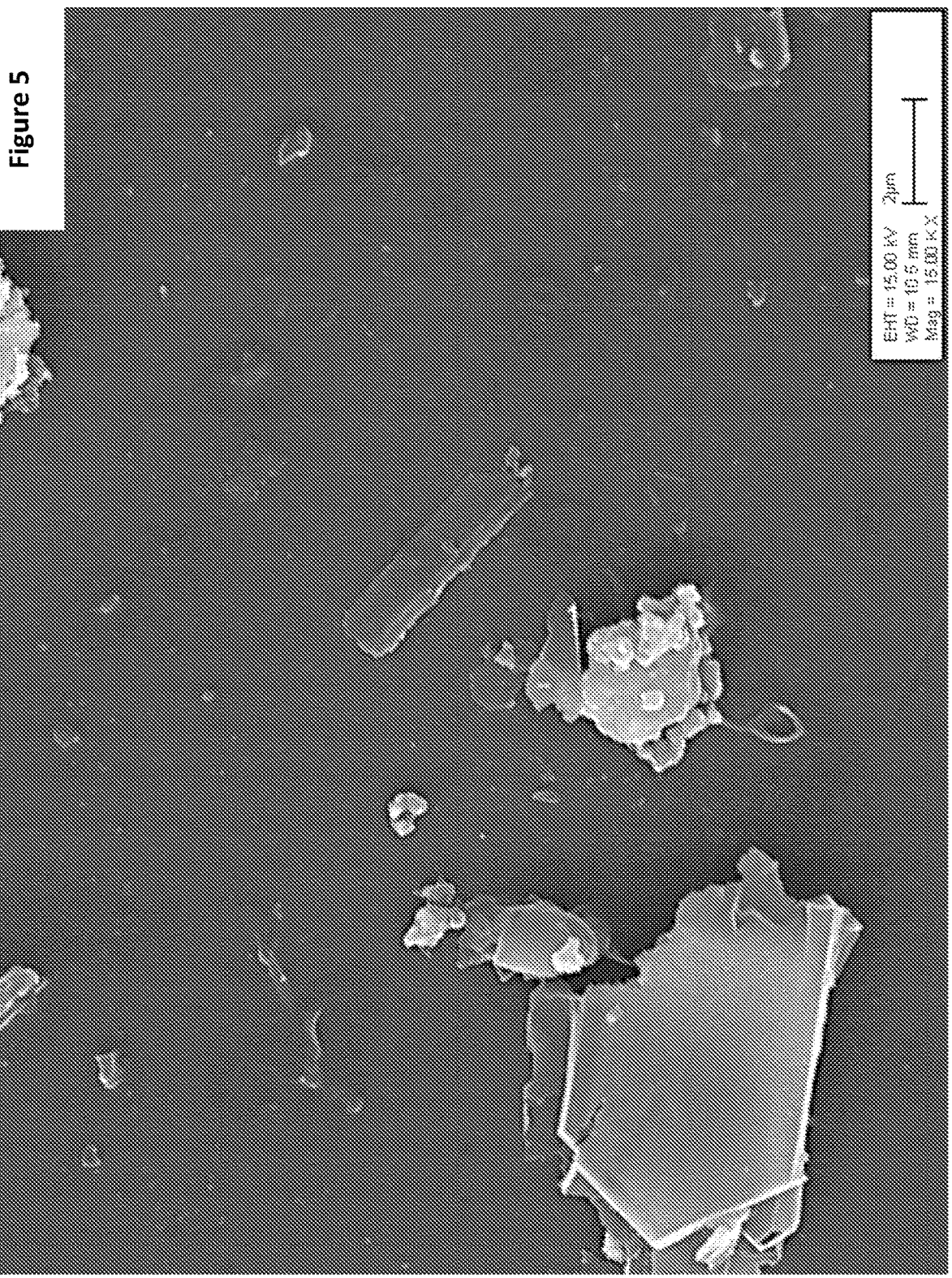
FIG. 5 shows an SEM image of ZnO micro particles obtained by agitation of the solution at a concentration of 5.17 M containing admixture-free nano-sized ZnO particles by agitation at the speed of 200 rpm which corresponds to insufficient agitation in lack of admixtures thereby failing to cause sufficient Reynolds' number.
Figure 6:
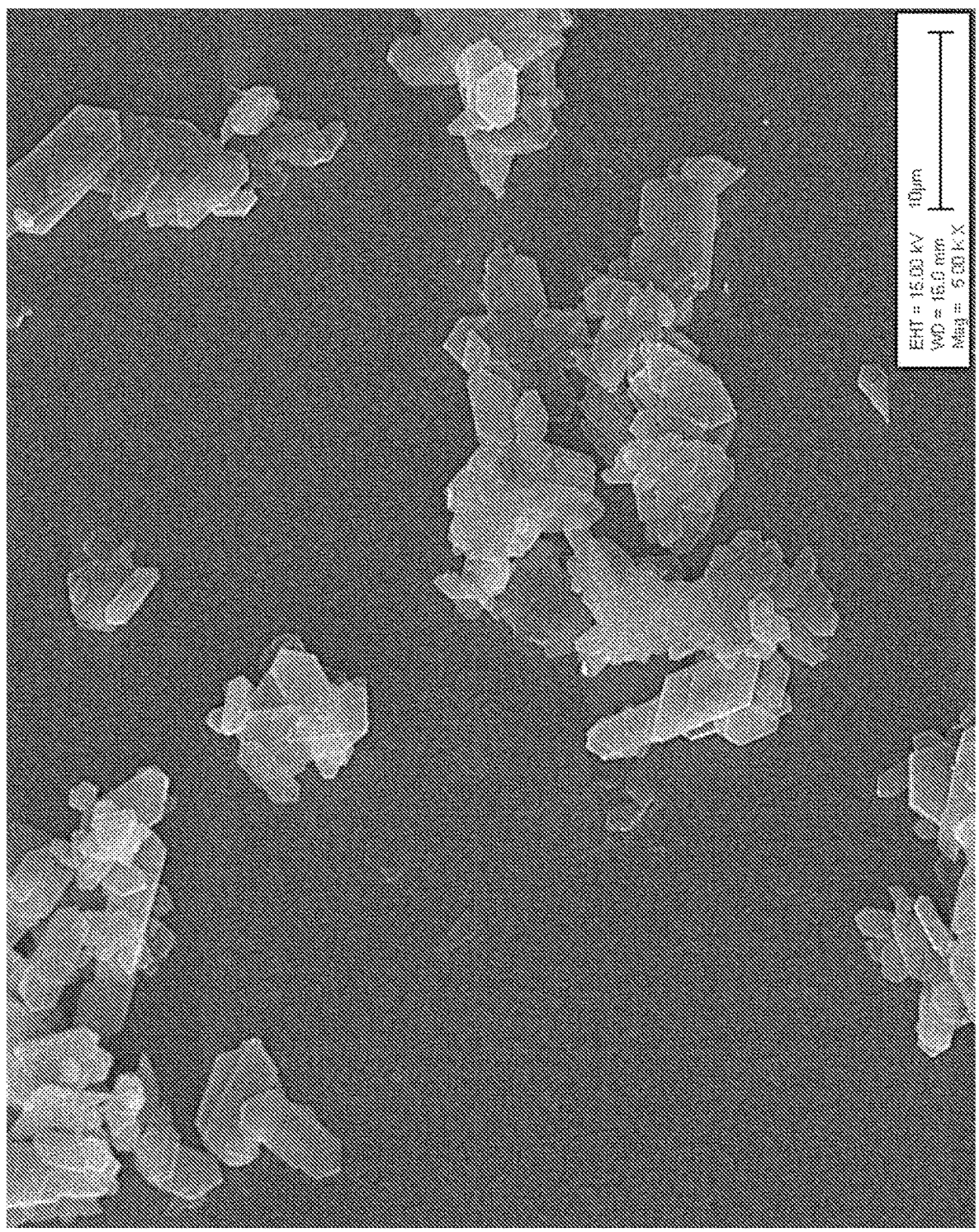
FIG. 6 shows an SEM image of hexagonal ZnO micro particles obtained with the method according to the present invention, by agitation of the solution at a concentration of 5.17 M containing admixture-free nanosized ZnO particles by agitation at the speed of 500 rpm, which corresponds to the optimum agitation rate due to the Reynolds' number achieavable thereby.
Figure 7:
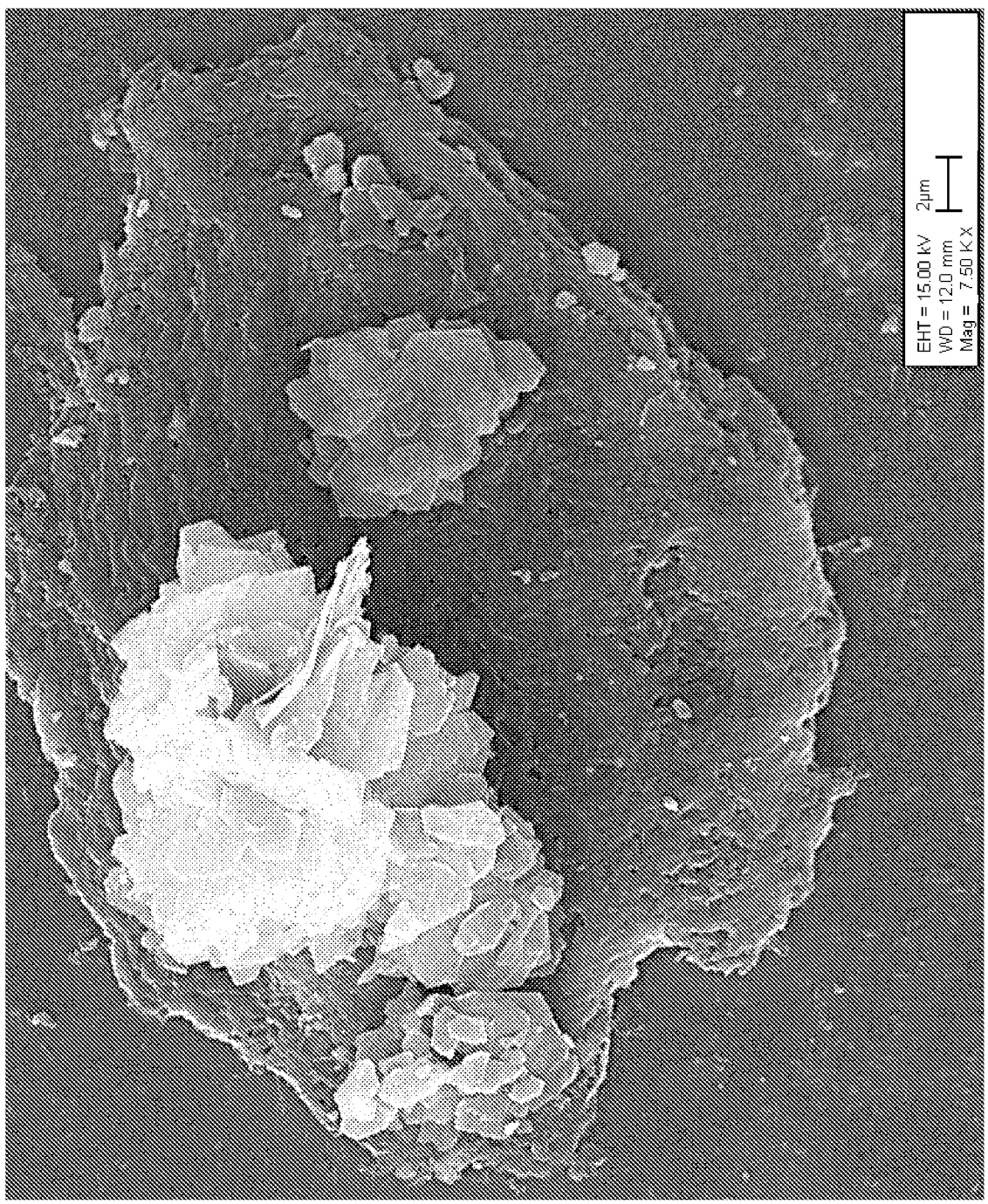
FIG. 7 shows an SEM image of ZnO micro particles obtained by an initial ZnO concentration of 5.17 M without admixtures, at an agitation speed of 1000 rpm which corresponds to a value of Reynolds' number (i.e., 11000) over the maximum acceptable value of 10000 at which the platelets start to deform.

FIGS. 4 and 5 show that the hydrodynamic forces, which are required for the intended platelet shape, cannot be achieved without sufficient agitation (i.e. low values of Reynolds' number). On the other hand, FIG. 6 shows that the ZnO micro particles obtained from the solution agitated at the speed of 500 rpm in the optimum range of 225-900 rpm have hexagonal platelet shapes both of which speeds correspond to sufficient extents of Reynolds' number (i.e., between 2500 and 10000). FIG. 7 shows that the micro platelets lose their form and disintegrate as a result of over-agitation (i.e. Reynolds' numbers beyond the range defined in the present description). As illustrated in these figures, the Reynolds' number achieved via the mixing speed plays a vital role in formation of polygonic ZnO micro platelets which are thin and thereby having specific surface areas larger than 25 and even 30 m2/g. FIGS. 8 to 13 clearly illustrate that majority of the ZnO platelets produced by doping the ZnO nano particles with admixtures present large surface area (>=30 m2/g) that ensures high covering capabilities.

Accordingly, the present invention further proposes a product including polygonic Zinc oxide platelets having a median specific surface area of more than 25 square meters per gram, controlled obtainment of which is rendered possible with the above disclosed method according to the present invention.

The product can be a cosmetic product for being brought into direct contact with the human skin, the platelets including Silver as a further metal in elementary form, or in form of one or more oxides and/or one or more salts thereof. Silver provides antimicrobial properties to the product.

The platelets can include one or more of Aluminium, Gallium and Indium, as a further metal in elementary form, or in form of one or more oxides and/or one or more salts thereof. Tailor-made electrical conductivity properties can be provided to the product by doping said materials thereinto in various amounts.

The platelets can include one or both of Iron and Cobalt as a further metal in their elementary form, or in form of one or more oxides and/or one or more salts thereof. Photocatalytic and/or magnetic properties for specific uses can be added to the product by employing various amounts of these materials therein.

In view of the above mentioned aspects, the present invention provides solution to the shortcomings encountered in the prior art. The present invention further provides a method enabling the obtainment of ZnO microplatelets with controlled agglomeration of nanoparticles so that specific size and morphology, thereby polygonal ZnO microplatelets with high specific surface area which are large enough for prevention thereof from penetrating into biological pores on the human or plant systems. Said high specific surface area (high surface area per unit mass of the product) can be formulated as light transmittance of 50% or more at a wavelength of 600 nm, which is achieved by the product according to the present invention. The term "platelets" can be interpreted as micron-thickness (i.e. micron-scale height) prismatic bodies essentially composed of primary nanoparticles.

What is claimed is:

1. A product comprising a plurality of polygonic zinc oxide platelets having a size in micron-scale and a median specific surface area of more than 25 square meters per gram, wherein the plurality of polygonic zinc oxide platelets are formed through agglomeration of a plurality of ZnO primary nanoparticles, and the plurality of polygonic zinc oxide platelets have a thickness providing a light transmittance of more than 30% at a wavelength of 600 nanometers.

2. The product according to the claim 1, wherein the product is a cosmetic product for being brought into direct contact with a human skin, the plurality of polygonic zinc oxide platelets comprising silver as a further metal in an elementary form, or in a form of one or more oxides and/or one or more salts of silver.

3. The product according to the claim 1, wherein the plurality of polygonic zinc oxide platelets comprise one or more of aluminium, gallium and indium, as a further metal in an elementary form, or in a form of one or more oxides and/or one or more salts of aluminium, gallium and indium.

4. The product according to the claim 1, wherein the plurality of polygonic zinc oxide platelets comprise one or both of iron and cobalt as a further metal in an elementary form, or in a form of one or more oxides and/or one or more salts of iron and cobalt.

5. A method for producing a product comprising a plurality of polygonic zinc oxide platelets having a size in micron-scale and a median specific surface area of more than 25 square meters per gram, wherein the plurality of polygonic zinc oxide platelets are formed through agglomeration of a plurality of ZnO primary nanoparticles, and the plurality of polygonic zinc oxide platelets have a thickness providing a light transmittance of more than 30% at a wavelength of 600 nanometers; the method comprising preparation of a medium comprising zinc or a plurality of compounds comprising zinc at a concentration within a range between 1.55 and 7.75 moles of zinc per liter of medium, in a medium suitable to substitute Zn ions by releasing free protons thereby forming a complex structure including Zn, agitation of the medium in a vessel at a temperature within a range between 50° C. and 320° C. for a duration up to 10 hours to obtain a suspension, filtering the suspension to obtain a filtrate comprising solid particles, drying the filtrate to obtain a dried filtrate, and calcination of the dried filtrate thereby obtaining the product;

wherein the agitation is performed with one or more radial flow impellers so that the Reynolds' number in the vessel is maintained higher than 2500 and lower than 10000.

6. The method according to claim 5, wherein the agitation is performed at a temperature within a range between 200° C. and 280° C.

7. The method according to claim 5, wherein the agitation is performed for a duration within a range between 45 and 75 minutes.

8. The method according to claim 5, wherein the filtering is performed in a further medium having a lower polarity relative to the medium used in the preparation of the medium comprising zinc or the plurality of compounds comprising zinc.

9. The method according to claim 5, wherein the drying of the filtrate is performed at a temperature below 65° C.

10. The method according to claim 5, wherein the calcination is performed at a temperature within a range between 200° C. and 700° C.

11. The method according to claim 5, wherein the medium comprises one or more of the compounds selected from the list consisting of glycerin, glycolates, ethylene glycol, 1,3 propanediol, tri-hydroxy benzene, tri-hydroxy benzoic acid, tri-hydroxy butane and tri-hydroxy pentane.

12. The method according to claim 5, wherein the agitation is performed using a shaft provided with a plurality of radial flow impellers distributed on the shaft.

13. The method according to claim 12, wherein a ratio obtained by a diameter of the plurality of radial flow impellers with respect to a shaft axis at a projection on the shaft, to a diameter of the vessel at a same projection on the shaft is between 0.3 and 0.4.

14. The method according to claim 5, wherein preparation of the medium comprises a zinc source of ZnO.

15. The method according to claim 14, wherein an impelling is performed using a shaft provided with the one or more of radial flow impellers distributed on the shaft.

16. The method according to claim 14, wherein a ratio obtained by a diameter of the plurality of radial flow impeller with respect to a shaft axis at a projection on the shaft, to a diameter of the vessel at a same projection on the shaft is between 0.3 and 0.4.

17. The method according to claim 5, wherein the medium comprises one of the further metals selected from the list consisting of aluminium, gallium, silver, indium, iron and cobalt as an admixture, wherein the further metal is in an elementary form, in a form of one or more oxides, and/or in a form of one or more salts of the further metal, and wherein an initial concentration of the admixture in the medium is between 0.01 and 20% (mol/mol) with respect to Zn.

18. The method according to claim 17, wherein an impelling is performed using a shaft provided with the one or more of radial flow impellers distributed on the shaft.

19. The method according to claim 17, wherein a ratio obtained by a diameter of the plurality of radial flow impeller with respect to a shaft axis at a projection on the shaft, to a diameter of the vessel at a same projection on the shaft is between 0.3 and 0.4.

20. The method according to claim 17, wherein preparation of the medium comprises a zinc source of ZnO.

* * * * *